United States Patent [19]

Goldberger

[11] Patent Number: 4,832,045
[45] Date of Patent: May 23, 1989

[54] BIOPSY INSTRUMENT

[76] Inventor: Robert E. Goldberger, 4 The Birches, Roslyn Estates, N.Y. 11576

[21] Appl. No.: 169,824

[22] Filed: Mar. 18, 1988

[51] Int. Cl.$^4$ .............................................. A61B 10/00
[52] U.S. Cl. .................................. 128/754; 128/305; 128/310
[58] Field of Search .................. 128/749, 751–754, 128/305, 305.1–310

[56] References Cited

U.S. PATENT DOCUMENTS

| | | | |
|---|---|---|---|
| 2,818,852 | 1/1958 | Kugler | 128/305 |
| 3,353,531 | 11/1967 | Armao | 128/305 |
| 3,512,519 | 5/1970 | Hall | 128/305 |
| 3,515,128 | 6/1970 | McEvoy | 128/305 |
| 3,583,390 | 6/1971 | Jascalevich | 128/305 X |
| 3,605,721 | 9/1971 | Hallac | 128/754 |
| 3,913,566 | 10/1975 | Lacey | 128/754 |
| 3,990,451 | 11/1976 | Gibbs | 128/754 X |
| 4,210,145 | 7/1980 | Nestor et al. | 128/305 |

Primary Examiner—Kyle L. Howell
Assistant Examiner—Angela D. Sykes

[57] ABSTRACT

A biopsy instrument for excising an elongated diamond-shaped tissue sample from a skin surface. The instrument has a handle with an elongated axis terminating at one end in a coaxially mounted diamond-shaped knife having a plurality of identical V-shaped cutters with downwardly sloping cutting blades. The cutters are contiguous to each other. The interior of the knife is recessed a predetermined distance inwardly of the V-shaped cutters. The inclined sharpened cutting blades cut in elongated diamond-shaped incision upon the application of axial pressure to the handle of the instrument. The remaining diamond-shaped lesions can then be easily sutured closed.

5 Claims, 2 Drawing Sheets

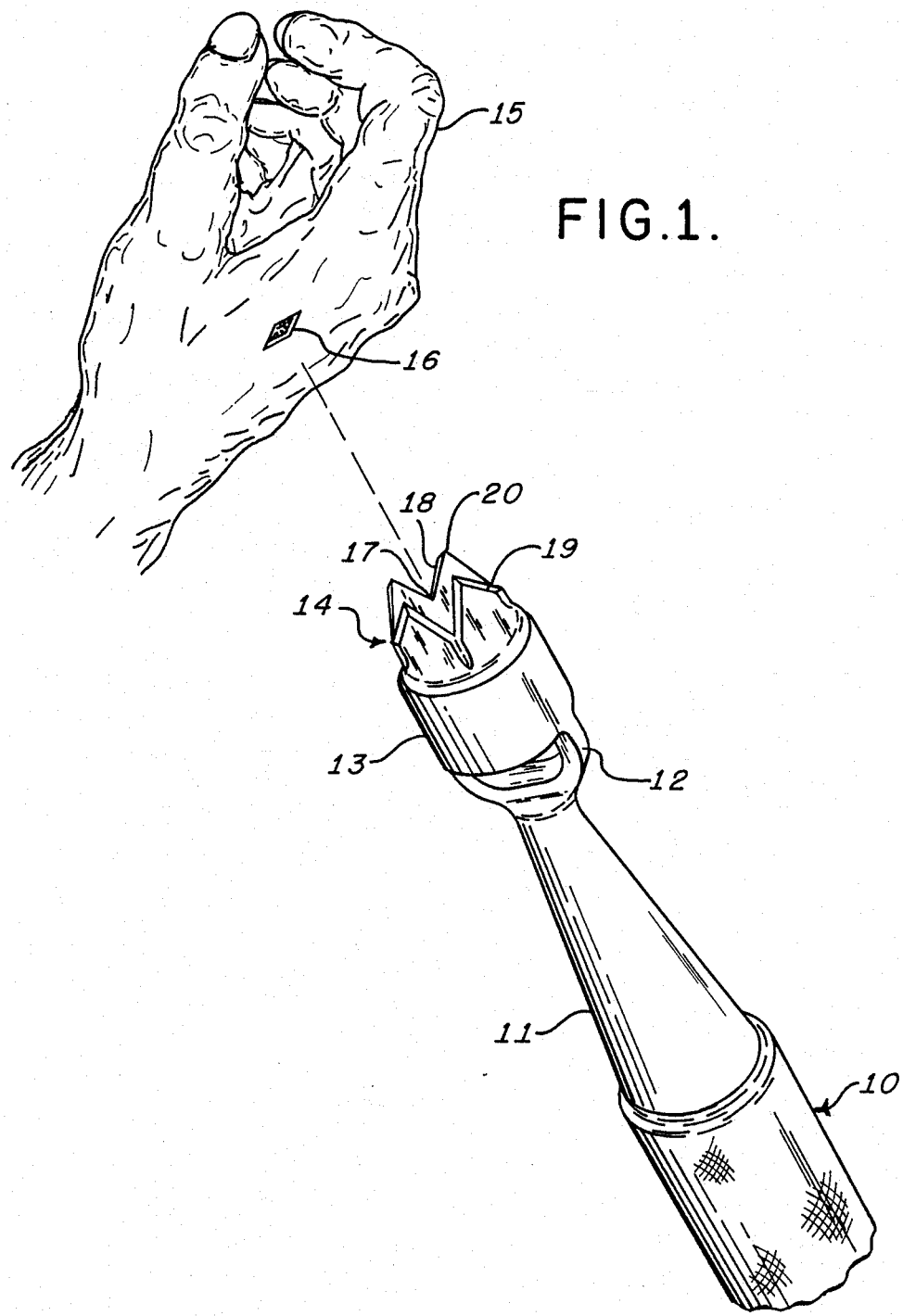

BIOPSY INSTRUMENT

BACKGROUND OF THE INVENTION

1. Field of the Invention

This invention relates to an improved biopsy instrument, and more particularly to a biopsy instrument which makes a narrow diamond-shaped incision which permits the removal of a sample of tissue, most often skin tissue and permits the incision to be more easily stitched or sutured closed leaving a scar that is superior cosmetically.

There are a number of instruments used to take tissue specimen from skin tissue. Most of the instruments use a circular cutting edge that is pushed into the surface of the skin and rotated to cut out a circular specimen of tissue. After the specimen is lifted out of the surface of the skin, a circular lesion or hole remains that is difficult to stitch or suture closed without leaving a scar.

2. Description of the Prior Art

There are a number of biopsy instruments in the prior art. In U.S. Pat. No. 4,210,145, a square surgical cutter is provided for use with removing scalp plugs in hair transplanting operations which will be unsuitable for biopsy sample tissues. In U.S. Pat. No. 2,818,852, there is provided a surgical instrument which is spring-loaded and contains a circular cutting device for removing tissue samples. Other patents, such as U.S. Pat. No. 3,515,128 and U.S. Pat. No. 3,512,519 provide skin biopsy punches which produce circular lesions and U.S. Pat. No. 3,353,531 provides an instrument with a specimen lifting means. However, these patents still leave lesions which are difficult to close.

SUMMARY OF THE INVENTION

Accordingly, the present invention provides a surgical biopsy instrument using a plurality of pointed, closely spaced cutting edges that are designed to cut a tissue sample which is diamond-shaped and elongated so that the resulting lesion or opening can be easily sutured closed without a noticeable scar remaining.

The invention includes at least four V-shaped cutting blades which are arranged adjacent to each other and in an elongated diamond shape pattern formed at the end of a cutting instrument so that the tissue specimen can be removed with only a downward non-twisting motion into the surface of the skin. Each of the cutting blades is sharply pointed and has downwardly sloping V-shaped cutting edges. Thus, as the instrument is pushed into the surface of the skin, the downwardly sloping edges cleanly cut the epidermis and dermis or skin tissue so that, upon the full insertion of the cutting blade into the skin, a tissue sample becomes detached or excised from the skin and can be easily removed for a biopsy. The resulting lesion or opening left in the skin after the tissue sample has been removed is a narrow or elongated diamond-shaped cut which can be easily sutured closed.

It is, therefore, an object of the present invention to provide a biopsy instrument which contains a plurality of cutting edges that are capable of cutting a narrow diamond-shaped opening.

It is another object according to the invention to provide a biopsy cutting instrument which is simple in design, easy to manufacture and reliable in operation.

Other objects and features of the present invention will become apparent from the following detailed description considered in connection with the accompanying drawings which disclose the embodiments of the invention.

In the drawings, similar reference characters denote similar elements throughout the several views.

BRIEF DESCRIPTION OF THE DRAWINGS

FIG. 1 is a perspective view of a person's hand showing a tissue sample having been removed leaving a diamond-shaped lesion in the surface of the skin;

FIG. 2 is an elevated perspective view of the cutting instrument according to the invention which has been applied to the hand of FIG. 1;

DESCRIPTION OF THE PREFERRED EMBODIMENT

Figure 3:
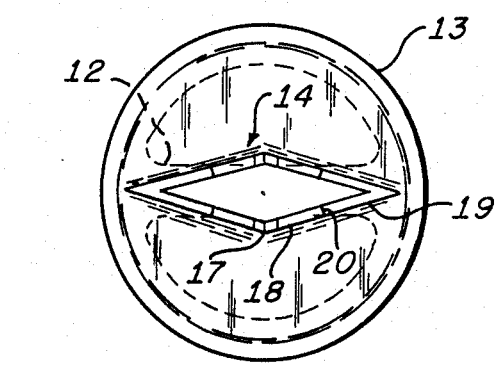
FIG. 3 is a top plan view of the cutting blades of the instrument of FIG. 2.
Figure 4:
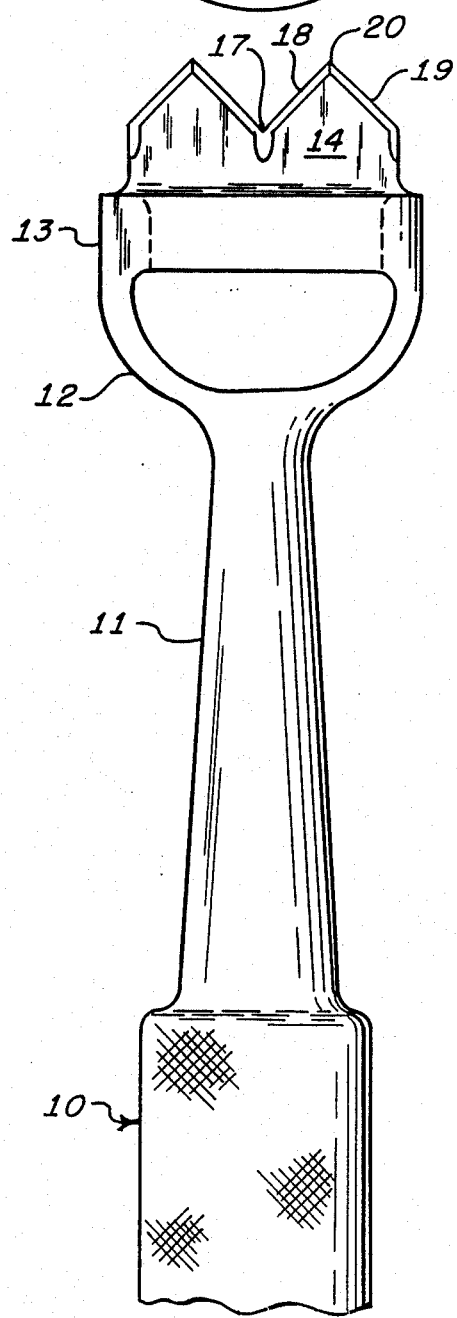
FIG. 4 is a side plan view of the biopsy instrument according to the invention.

Referring to FIGS. 1-4, there is shown the biopsy instrument 10 having a knurled handle, a shank portion 11, and a barrel-shaped receptacle end 13 supported on legs 12. At the top surface of receptacle end 13 are disposed four V-shaped cutting blades 14 comprised of a pair of downwardly sloping blades 18 and 19 which intersect at a point 20. Each of the V-shaped blades 14 connects to identically formed adjacent cutting blades 14 by means of blade transition 17. Each of the V-shaped blades 18 and 19 is bevelled to a sharp downwardly sloping edge and is preferably constructed of a non-corrosive metal such as surgical stainless steel or the like. Blades 14 are secured on the edge of barrel-shaped end 13 in a contiguous and continuous closed manner to form a narrow diamond-shaped pattern as shown in FIG. 3, so that there are preferably four points 20 and four sharp transition edges or areas 17.

In operation, the physician will direct the axis of surgical tool 10 perpendicular to the surface of the skin so that the four points 20 of blades 14 will initially contact the skin surface. When pressure is applied along the axis of instrument 10, the points will pierce through the surface of the skin and allow the downwardly extending blades 18 and 19 to cut through the skin. As the physician continues to urge the instrument further, the four sharp transition areas 17 cut through the surface of the skin to free up the four remaining corners of the elongated diamond-shaped specimen. The physician can then easily remove the specimen after the biopsy instrument is withdrawn. The narrow diamond-shaped opening that remains as shown in FIG. 1 can be easily pinched together or closed and either sutured or taped until it heals together.

The four transition areas 17 at the intersection of each of the V-shaped blades are particularly critical since they are designed to form a concave and continuous cutting area in order to cut through and separate the four corners of the tissue specimen after the surgical tool has been fully inserted.

In construction, the handle of the instrument is preferably knurled to provide a firm grip to the user. The handle, the shank and the head may preferably be constructed of aluminum or steel while the blades are preferably constructed of surgical stainless steel. The edges of each of the V-shaped cutters are preferably bevelled along their outside surfaces. The cutting edges may be made in a variety of different sizes to accommodate the user. Instruments producing a defect of diameters of 3, 4, 5, 6, 7, 8, and 10 mm are planned. Each of the four cutters 14 which have their transitional area 17 contiguous to each other are preferably identically shaped. The end 13 of the instrument which supports two or more cutters 14 has a diameter in area preferably larger than the area defined by the cutting blades so that the top surface of the cutting head will limit the depth of cut of the cutters into the surface of the skin.

The vertical distance or separation between cutter transition area 17 and the top surface of end 13 should be equal to the thickness of the skin. The height of blade points 20 above transition area 17 should be kept to a minimum while still providing a sufficient cutting incline for blades 18 and 19. The hollow interior of the knife is preferably recessed sufficiently to allow an epidermis sample to be collected within the blade after it has been excised.

For very small surgical instruments, it is possible to use only two V-shaped cutters so that the blade can be slightly bent bend in the middle to form a diamond-shaped opening with one other adjacently mounted blade that is also bend in the middle. It is also possible to use more than four cutters 14 as long as the cutters are contiguous with one another in a diamond-shaped pattern.

While only a single embodiment of the present invention has been shown and described, it is obvious that many modifications may be made thereto without departing from the spirit and scope of the claims.

What is claimed is:

1. An instrument for cutting an elongated diamond-shaped lesion in the surface of the skin for permitting the removal of an elongated diamond-shaped biopsy sample comprising:

a handle having an elongated axis terminating at one end in a flat, blade-receiving surface;

a coaxially mounted diamond-shaped knife having two pairs of identically shaped cutters adjacently disposed on said blade-receiving surface, each cutter being V-shaped and having a pair of downwardly sloping cutting blades which intersect and are contiguous with the downwardly sloping cutting blades of the adjacent V-shaped cutter, the adjacent cutter of each pair intersecting at an obtuse angle, each pair of cutters joining the second pair of cutters at an acute angle to define a four cutter, eight bladed closed diamond-shaped knife, the interior of said knife defined as the area surrounded by said blades being recessed a predetermined distance inwardly of said V-shaped cutters, said downwardly sloping cutting blades of each of said cutters cutting an elongated diamond-shaped incision upon the application of axial pressure to the handle of said instrument.

2. The instrument as recited in claim 1, wherein each of the downwardly sloping cutting blades intersects in a sharp transition area with the cutting edge of the adjacent cutter.

3. The instrument as recited in claim 2, wherein each of said cutting blades of said knife is bevelled to a sharp blade.

4. The instrument as recited in claim 2, wherein said flat blade-receiving surface is larger in diameter than the diamond-shaped knife to serve as a limiting surface to control the depth of the incision.

5. The instrument as recited in claim 4, wherein said flat blade-receiving surface is separated from said transition area by a distance equal to at least the thickness of the skin.

* * * * *